US00PP24386P2

(12) United States Plant Patent
Stemkens

(10) Patent No.: US PP24,386 P2
(45) Date of Patent: Apr. 15, 2014

(54) ***VERBENA* PLANT NAMED 'VEAZ0013'**

(50) Latin Name: *Verbena×hybrida*
Varietal Denomination: VEAZ0013

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 150 days.

(21) Appl. No.: 13/507,401

(22) Filed: Jun. 25, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Howard Locker
(74) *Attorney, Agent, or Firm* — Joshua L. Price

(57) ABSTRACT

A new *Verbena* plant named 'VEAZ0013' particularly distinguished by the creamy light yellow-green flower color, single to semi-double flower habit on a semi-upright plant habit.

2 Drawing Sheets

Latin name of the genus and species of the plant claimed: *Verbena×hybrida.*

Varietal denomination: 'VEAZ0013'.

BACKGROUND OF THE NEW PLANT

The present invention comprises a new *Verbena*, botanically known as *Verbena×hybrida*, and hereinafter referred to by the variety name 'VEAZ0013'.

'VEAZ0013' is a product of a planned breeding program. The new cultivar has creamy light yellow-green flower color, single to semi-double flower habit on a semi-upright plant habit.

'VEAZ0013' originated from an open-pollinated hybridization made in August 2007, in a greenhouse in Enkhuizen, The Netherlands. The female parent was the unpatented, plant designated 'KO399-2' with a light rose flower color and a more trailing plant habit than 'VEAZ0013'. The seed was sown in February 2008.

'VEAZ0013' was selected as one flowering plant within the progeny of the stated cross in August 2008 in a greenhouse in Enkhuizen, The Netherlands.

The first act of asexual reproduction of 'VEAZ0013' was accomplished when vegetative cuttings were propagated from the initial selection in August 2008, in a greenhouse in Enkhuizen, The Netherlands.

BRIEF SUMMARY OF INVENTION

Horticultural examination of plants grown from cuttings of the plant initiated in August 2008, and continuing thereafter, has demonstrated that the combination of characteristics as herein disclosed for 'VEAZ0013' are firmly fixed and are retained through successive generations of asexual reproduction.

'VEAZ0013' has not been observed under all possible environmental conditions. The phenotype may vary significantly with variations in environment such as temperature, light intensity and day length.

A Plant Breeder's Right for this cultivar was applied for in Community Plant Variety Office on Jun. 27, 2011 (11/1600) and in Canada on Nov. 1, 2011 (11-7417). 'VEAZ0013' has not been made publicly available more than one year prior to the filing of this application.

The following traits have been repeatedly observed and are determined to be basic characteristics of the new variety. The combination of these characteristics distinguishes this *Verbena* as a new and distinct variety

BRIEF DESCRIPTION OF THE PHOTOGRAPHS

The accompanying photographic drawings show typical flower and foliage characteristics of 'VEAZ0013' with colors being as true as possible with an illustration of this type. The first photographic drawing shows a flowering plant of the new variety, and in the second photo, a close-up of the flowers.

DETAILED BOTANICAL DESCRIPTION

The plant descriptions and measurements were taken in early June, 2012 under natural light. These plants were approximately 12 weeks of age, and growing in 30 cm wide×1 meter long window boxes, outside in full sun, in Enkhuizen, The Netherlands.

The aforementioned photographs were taken in April 2011. These plants were approximately 12 weeks of age, growing in a greenhouse trial in Enkhuizen, The Netherlands in 10 cm pots.

Color references are made to The Royal Horticultural Society Colour Chart (R.H.S.) 2001.

TABLE 1

DIFFERENCES BETWEEN THE NEW VARIETY 'VEAZ0013' AND THE MOST SIMILAR VARIETY: Corsage White Improved (unpatented)

| | 'VEAZ0013' | 'Corsage White Improved' |
|---|---|---|
| Flower color | creamy light yellow-green | creamy white |
| Plant habit | more semi-upright | more trailing |

Plant:

*Form, growth and habit.*—Initially upright and then with semi-trailing growth habit.

*Plant height* (*cm*).—13.0 cm.
*Plant height* (*inflorescence included*) (*cm*).—17.0 cm.
*Plant width* (*cm*).—32.0 cm.

Roots:
*Number of days to initiate and produce roots.*—10-14 days at about 22 degrees C.
*Type*.—Fine, fibrous, free branching.
*Color*.—RHS N155B but whiter.

Foliage:
*Arrangement*.—Opposite.
*Immature, leaf color, upper surface*.—RHS 137C.
*Lower surface*.—RHS 138B.
*Mature, leaf color, upper surface*.—RHS 137B.
*Lower surface*.—RHS 138B.
*Length* (*cm*).—4.5 cm.
*Width* (*cm*).—3.0 cm.
*Shape*.—Ovate.
*Base shape*.—Shortly attenuate.
*Apex shape*.—Obtuse.
*Margin*.—Irregularly crenate, sinuate.
*Texture, upper surface*.—Heavily hirsute.
*Lower surface*.—Heavily hirsute.
*Color of veins, upper surface*.—RHS 145B.
*Color of veins, lower surface*.—RHS 145B.
*Pattern of veining*.—Pinnate.
*Petioles color*.—RHS 145B.
*Petioles length* (*cm*).—0.4 cm.
*Petiole width* (*cm*).—0.2 cm.
*Texture*.—Heavily hirsute.

Stem:
*Quantity of main branches per plant.*—6.
*Color of stem*.—RHS 143C.
*Stem length* (*cm*).—About 9.0 cm.
*Stem width* (*cm*).—0.3 cm.
*Length of internodes* (*cm*).—0.4 cm.
*Texture*.—Heavily hirsute, pilose, glandular hairs.

Peduncle:
*Color of peduncle*.—RHS 143C.
*Length of peduncle* (*cm*).—3-4.0 cm.
*Peduncle diameter* (*cm*).—0.2 cm.
*Texture*.—Heavily hirsute, pilose, glandular hairs.

Inflorescence:
*Type*.—Umbel-like, actually a spike, umbrella-shaped to roughly semi-spherical.
*Blooming habit*.—Flowers continuously.
*Lastingness of individual blooms on the plant*.—About 6 days in the greenhouse.
*Fragrance*.—Slight.
*Number of inflorescences per plant.*—20.
*Horizontal diameter of inflorescence* (*cm*).—6.0 cm.
*Depth of inflorescence* (*cm*).—4.5 cm.
*Number of florets per inflorescence* (*including any buds at the time*).—Average 35.

Bud (just when opening/showing color):
*Color*.—RHS 154D.
*Length* (*cm*).—0.8 cm.
*Width* (*cm*).—0.1 cm.
*Shape*.—Mainly tube-shaped with a bulbous end.

Floret:
*Form and type*.—Sessile; salverform, composed of 5 partly fused petals with a base of a narrow tube and sometimes a semi-double composed of 6-7 petals.

Immature flower:
*Main color upper surface*.—Between RHS 150C and RHS 150D.
*Main color lower surface*.—RHS 154D.

Mature flower:
*Color, upper surface*.—RHS 150D.
*Color, lower surface*.—Lighter than RHS 150D.
*Floret diameter* (*cm*).—2.0 cm.
*Floret length* (*cm*).—2.1 cm.
*Petal length* (*cm*).—0.95 cm.
*Petal width* (*cm*).—1.0 cm.
*Shape*.—Orbicular.
*Apex shape*.—Rounded.
*Margin*.—Entire; undulate.
*Petal texture, upper surface*.—Papillose.
*Lower surface*.—Papillose; hirsute, some glandular hairs.
*Corolla tube length* (*cm*).—1.6 cm.
*Corolla tube width* (*cm*).—0.2 cm.
*Corolla tube color inside*.—RHS 154D.
*Tube color outside*.—RHS 154D.
*Corolla texture, inside*.—Papillose.
*Outside*.—Puberulous.
*Throat hair color*.—Closest to RHS 155D.

Calyx:
*Type*.—Five sepals whose margins are fused to each other along their length, with a transparent membrane of less than 0.1 cm in width and with one smaller sepal attached to the base of the calyx.
*Color of sepals*.—RHS 138B.
*Length of sepals* (*cm*).—1.3 cm.
*Width of sepals* (*cm*).—0.2 cm.
*Sepal shape*.—Linear.
*Apex shape*.—Apiculate.
*Margins*.—Entire.
*Texture*.—Hisute; glandular hairs.

Reproductive organs:
*Gynoecium*.—Pistil: 1. Pistil length (cm): 1.6 cm. Style color: RHS N144D. Style length (cm): 1.5 cm. Stigma color: RHS 141C. Ovary color: RHS 144B. Ovary length (cm): 0.1 cm. Ovary width (cm): 0.1 cm.
*Androecium*.—Stamens: Anthers and filaments fused to upper half of corolla tube; four anthers with two pollen sacs per anther. Color of filaments: RHS 154D. Filament length (cm): 0.2 cm. Anther color: RHS 154C. Anther length (cm): 0.15 cm. Pollen amount: None, as the anthers are all dried. Fertility/seed set: Has not been determined to date. Disease/pest resistance: Has not been determined to date.

What is claimed is:

1. A new and distinct variety of *Verbena* plant named 'VEAZ0013' substantially as illustrated and described herein.

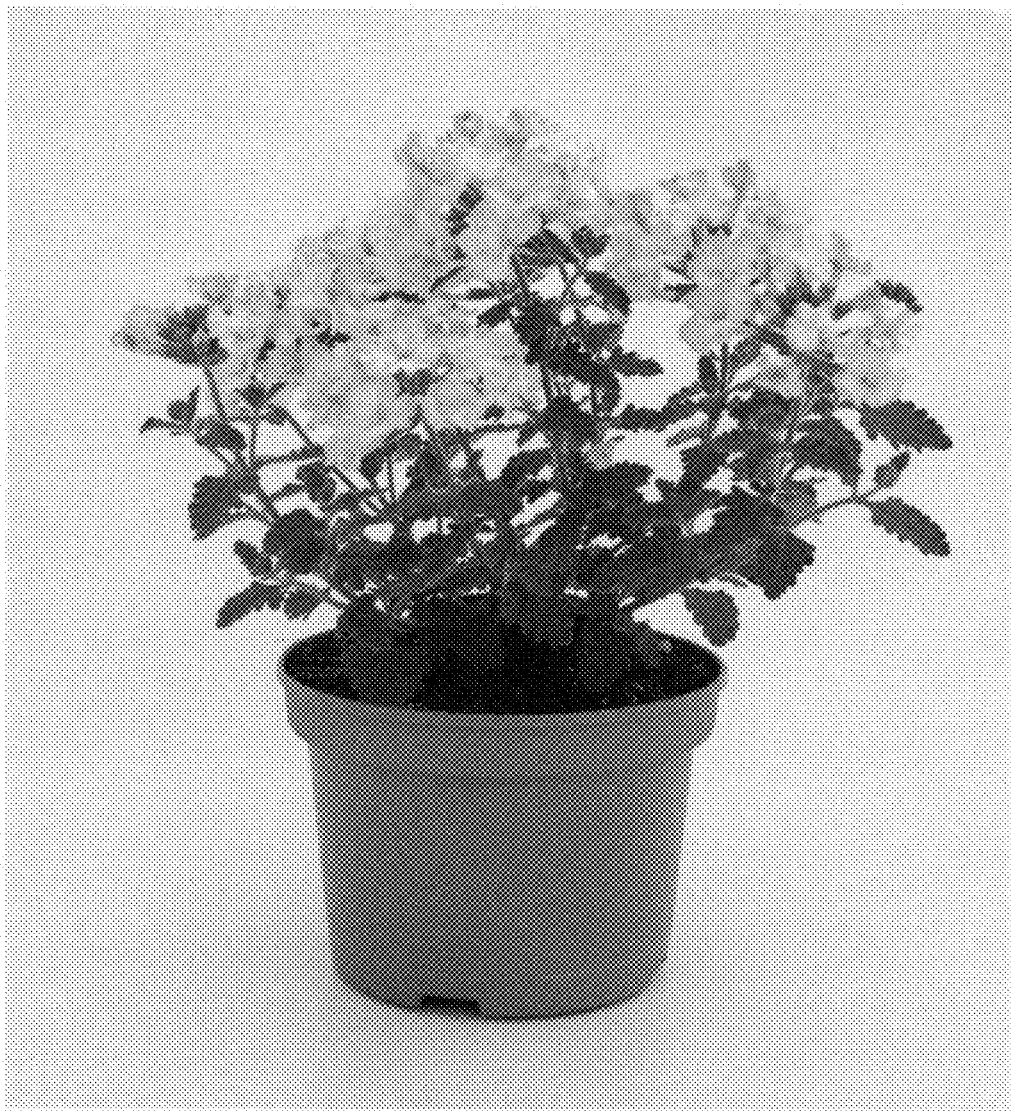

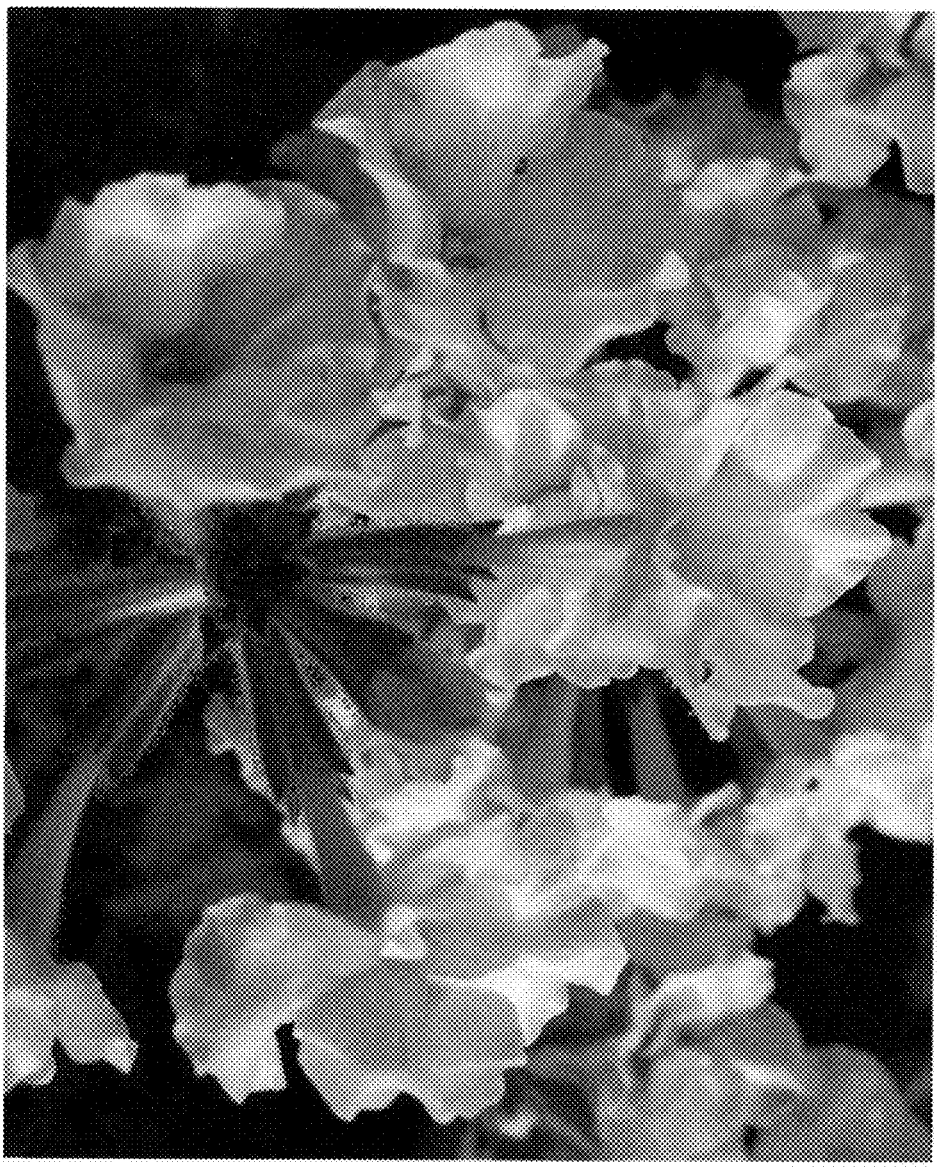

* * * * *